(12) United States Patent
Gundersen (10) Patent No.: US 8,926,212 B2
(45) Date of Patent: Jan. 6, 2015

(54) PAD WITH INTERNAL CHAMBER AND OPENING MECHANISM

(75) Inventor: Dag H. Gundersen, TolvsrØd (NO)

(73) Assignee: PadTech AS, Fornebu (NO)

( * ) Notice: Subject to any disclaimer, the term of this patent is extended or adjusted under 35 U.S.C. 154(b) by 0 days.

(21) Appl. No.: 14/240,407

(22) PCT Filed: Aug. 24, 2012

(86) PCT No.: PCT/EP2012/066511
§ 371 (c)(1),
(2), (4) Date: Apr. 9, 2014

(87) PCT Pub. No.: WO2013/026924
PCT Pub. Date: Feb. 28, 2013

(65) Prior Publication Data
US 2014/0208532 A1    Jul. 31, 2014

(30) Foreign Application Priority Data
Aug. 25, 2011   (NO) .................................. 20111159

(51) Int. Cl.
| B43K 5/14 | (2006.01) |
| A45D 37/00 | (2006.01) |
| A45D 34/04 | (2006.01) |
| A61F 13/40 | (2006.01) |
| A61F 13/00 | (2006.01) |

(52) U.S. Cl.
CPC ............... *A45D 37/00* (2013.01); *A45D 34/04* (2013.01); *A61M 35/006* (2013.01); *A45D 2200/1018* (2013.01); *A45D 2200/1045* (2013.01); *A61F 2013/0017* (2013.01)
USPC .................... 401/205; 401/133; 401/7; 604/3

(58) Field of Classification Search
USPC ................. 401/132–135, 7, 8, 196, 205, 206; 604/3
See application file for complete search history.

(56) References Cited

U.S. PATENT DOCUMENTS

| 5,380,110 A * | 1/1995 | Festa .............................. 401/132 |
| 7,950,864 B2 * | 5/2011 | Bauer et al. ................... 401/132 |

(Continued)

FOREIGN PATENT DOCUMENTS

| DE | 20011706 A | 9/2000 |
| DE | 202004017915 A | 1/2005 |

(Continued)

*Primary Examiner* — David Walczak
(74) *Attorney, Agent, or Firm* — Christian D. Abel (57) ABSTRACT

A device for applying at least one product at a desired surface, for instance a human's skin. The device comprises several layers 1-6, where an impermeable front layer (1) and an impermeable utility layer (6) together with a contact layer (2) will form the outer surfaces of the device (D), between which contact layer (2) and utility layer (6) are arranged a valve layer (3), a top layer (4) and a bottom layer (5). The top layer (4) and bottom layer (5) are connected to each other through a weld (11) in order to form a storage chamber (8) to accommodate a product. Furthermore, the valve layer (3) and top layer (4) are provided with a plurality of incisions or indentations (9a, 9b), where the incisions or indentations (9a) of the valve layer are welded to corresponding incisions or indentations (9b) of the top layer to form an opening mechanism in the device (D), where the device (D) is opened when the valve layer (3) is moved relatively to the top layer (4).

12 Claims, 5 Drawing Sheets

(56) References Cited

U.S. PATENT DOCUMENTS

| | | | |
|---|---|---|---|
| 8,157,464 B2 * | 4/2012 | Prax | 401/133 |
| 8,262,305 B2 * | 9/2012 | Lam et al. | 401/133 |
| 8,534,947 B2 * | 9/2013 | Prax | 401/133 |
| 2005/0284777 A1 | 12/2005 | Wilkman | |
| 2007/0048063 A1 | 3/2007 | Bauer et al. | |
| 2010/0239353 A1 | 9/2010 | Prax | |

FOREIGN PATENT DOCUMENTS

| | | |
|---|---|---|
| GB | 2469511 A | 10/2010 |
| WO | 2010002256 A | 1/2010 |
| WO | 2010019048 A | 2/2010 |

* cited by examiner

PAD WITH INTERNAL CHAMBER AND OPENING MECHANISM

The present invention relates to a device for applying at least one product to a desired surface. More particularly the present invention relates to a pad accommodating at least one product, where the pad is comprised of several material layers that are joined together and provided with an opening mechanism.

There are several different methods available today for applying various products on a desired surface, for instance on a human's skin. The product can be a liquid or a colloidal substance or a combination thereof.

For instance the product can be applied to a surface by the user simply placing the product from a bottle or tube on their hand and then manually spreading the product on the desired surface. This method is the most inexpensive, but it is also inefficient, messy and may result in an uneven application of the product. Furthermore, the bottles or tubes contain a fairly large quantity of the product and can therefore be inconvenient for the user to carry around.

One other method is to have separate bottles and applicator elements. The applicator element will soak up some of the product when they are brought into contact with each other, whereby the user uses the applicator element to disperse the product over a desired spot or surface. This method may result in spillage when applying the product to the applicator element, and some of the product may also be wasted as the applicator element itself will absorb some of the product. A further problem with this method is that the product to be applied may come in contact with the user's hands, which is not desirable, especially if the product is irritating for the skin.

Yet another method for applying a product on a desired surface is to use a disposable or single-use applicator which is supplied with a pre-determined quantity of the product. Such applicators are manufactured from a disposable material substantially fully infused with the appropriate product, for example, a cleansing cream, and sealed in a container. This solution is relatively costly, since this often results in more of the cosmetic product being applied to the sheet of material, than is actually required. The applicator may also be so infused with the product to be applied that it will result in uneven application of the product on the desired surface. It will also be very difficult to control the amount of product transferred from the applicator to the skin, increasing the chance of excessive application of the product.

The above mentioned products can for instance be a liquid, such as wound cleansing agent, special cleansing liquid for various purposes such as, nail varnish, varnish remnants, glue remnants etc. and the colloidal substances can for instance be shoe cream, cosmetics, moisture creams, cleansing creams, self-tanning creams, various gel products for personal hygiene, soap etc. Furthermore, the product can be pharmaceutical products, such as pain relief, anti-itching agents etc.

A common feature of the applicators shown in the prior art is that they are not economical. Neither are they able to control the application of a product onto a surface.

Many of the known applicators will also have a tendency to leak and/or to desiccate after the applicator has been stored for a while. Due to this, the applicators are often manufactured from materials that are relatively thick and stiff, which may cause an irritation, a rash etc. on the surface to which the product is applied, especially if the surface is sensitive, for instance if the applicator is used to apply the product to human skin.

US 2005/0284777 A1 discloses a wipe package, where the wipe package includes an impregnated wipe, a sealed package containing the impregnated wipe and having an exterior surface and internal formulary reservoir to provide additional formulary to the impregnated wipe and at least one region on the exterior surface to secure the package to a user's hand or finger when using the impregnated wipe. The sealed package includes a front sheet, a first rear sheet having an interior surface and an exterior surface, and a second rear sheet. The impregnated wipe is secured to an interior surface of the first rear sheet, and at least the front sheet and the first rear sheet seal the impregnated wipe. The formulary reservoir is placed adjacent to the impregnated wipe to provide additional formulary.

US 2010/0239353 A1 discloses a disposable fluid applicator, where the fluid applicator has a reservoir with a first membrane and a second membrane. Said reservoir contains a fluid to be dispensed. Said first membrane of the reservoir has perforations and is covered by a permeable and/or absorbent spreader. A removable tab assembly is disposed between said spreader and said first membrane of the reservoir that seals said reservoir. When the tab is pulled from between said spreader and said first membrane of the reservoir the reservoir becomes unsealed allowing the fluid contained inside the reservoir to flow out through an opening in the first membrane into and through the spreader where the fluid can be applied to a desired surface.

GB 2.469.511 A discloses a wiping mitt, where the wipe contains a fluid in a container or package to which is attached a releasing or rupturing strip. Pulling the strip releases the fluid into the wipe. The wipe is constructed from first and second external wiping layers and a waterproof barrier layer interposed between the fluid container and the second wiping layer. The barrier layer prevents migration of the fluid to the second wiping layer which remains dry whilst the fluid wets the first wiping layer. All three layers are joined together around their edges, preferably by ultrasonic welds.

It is therefore an object of the present invention to provide a device which on the one hand will not leak during storage and transportation, and on the other hand will be soft enough to prevent irritation and/or damage to a surface on which the device is used.

A further object of the present invention is to provide an economical device for containing and dispensing a liquid or substance to a desired surface in a convenient, uniform and simple manner.

A further object of the present invention is to provide a device which will not soil the user during use of the device.

These objectives are achieved with a device for applying a product onto a desired surface according to the invention as defined in the enclosed independent claim, where embodiments of the invention are given in independent claims.

According to the present invention it is provided a device which can apply a product, such as a liquid(s) or colloidal substance(s) in a controlled manner onto a desired surface, for instance a human's skin, where the device comprises several material layers that are jointed in appropriate ways in order to create a liquid tight device. Each of the layers of the device will then have its own specific function.

A typical device according to the present invention may for example consist of six different layers, where a front layer and a utility layer will form the outer protective surfaces of the device. The front layer and the utility layer will then be welded over a part of their outer periphery, forming a partly closed device. Furthermore, the material that the front layer and utility layer are manufactured from will be dependent on the product that is contained in the device; for instance the front layer and the utility may layer be manufactured from an impermeable or substantially impermeable material if the product is a product with low viscosity, so that the device can be transported and/or stored without the risk of the product leaking from the device, or without the risk of the user's hands being soiled during use. A valve layer, top layer and a bottom layer will then faun an internal chamber inside the device that accommodates the product to be applied, where these layers in addition will form an opening mechanism in the device.

However, a person skilled in the art would understand that the device also may be comprised of fewer or more layers, where the number of layers will depend on the specific use of the device, the product to be contained in the device, the material from which the different layers are manufactured from etc.

According to an embodiment of the present invention, the device is comprised of a front layer, a contact layer, a valve layer, a top layer, a bottom layer and a utility layer. In addition, the device may be provided with holding means, for instance a pocket layer that can be joined to the utility layer in appropriate ways.

The front layer may be manufactured from a material with a certain degree of elasticity, for instance an elastic film, a non-woven or laminated material or materials, or a combination of different materials, whereby the front layer may serve the following purposes:
- to protect and keep clean a contact layer laying beneath the front layer until the device is to be used,
- the front layer can be turned over and around the outer periphery of the device in order to create a soft edge around the periphery of the device,
- the front layer can be turned back again over the contact layer when the device is used, in order to cover over the moisture surface of the contact layer, so that the device can be temporarily "stored" before it is thrown away, and
- the front layer forms a fluid tight connection with the utility layer whereby two or more liquids can be mixed between the two layers before the front layer is turned over and around the outer periphery of the device.

The contact layer is the layer that is in contact with the surface to which the product contained in the device is to be applied, whereby the material that the contact layer is manufactured from must be chosen from the following properties:
- the specific area of utilization for the device. The contact layer will be manufactured from a much softer material if the device is to be used to apply a product around the eyes than if the device is to be used to apply a product to someone's feet,
- the material's through-flow and distribution ability. A liquid with high viscosity (for instance a cream) will generally need a more open material structure than a liquid with low viscosity (for instance a make-up remover).

The contact layer can therefore be manufactured from a non-woven material, cotton, viscose, other suitable material(s) or even combinations thereof.

In some cases the contact layer may be comprised of several material layers in order to obtain the above mentioned functions.

The valve layer is the layer that is moved relative to the top layer before the device is to be used, where this will result in a plurality of through-going openings being created in a storage chamber in the device that accommodates the product to be applied onto the specific surface.

Furthermore, as the valve layer is to be opened before the device according to the present invention is to be used, the surface of the valve layer is cut with a knife, laser or ultrasound in order to provide a plurality of incisions or indentations in the valve layer. These incisions or indentations will provide flaps or tags in the surface of the valve layer, where the flaps or tags will have a mainly equal form or pattern, for instance a drop shaped form.

All of the flaps or tags will be arranged in one or more lines at the surface of the valve layer, and will have an equal partition distance in the direction the valve layer is moved.

The flaps or tags of the top layer are connected together with corresponding flaps or tags provided in the valve layer. The connected flaps or tags of the two layers (top layer and valve layer) will thereby provide the plurality of through-going openings in the storage chamber when the valve layer is moved relative to the top layer, prior to the use of the device according to the present invention.

The valve layer is normally manufactured from a film with good barrier characteristics or properties, often with a thin sheet of aluminium in the middle. The surface of the valve layer that is facing the top layer may for some materials be provided with so-called "peeling properties", which will help in opening the incisions or indentations provided in the valve layer and the top layer, but at the same time prevent the rest of the valve layer and the top layer from being ripped apart, when the valve layer and the top layer are moved relative to each other. A person skilled in the art will know how these properties can be obtained and therefore this is not discussed any further.

The top layer is the layer that forms the upper or outer surface in the storage chamber for the product that is accommodated in the device. This layer is also provided with a plurality of incisions or indentations, where this will create flaps or tags in the top layer. As in the valve layer these incisions or indentations are provided by using a knife, laser or ultrasound.

The top layer is normally manufactured from a film with good barrier characteristics or properties, often with a thin sheet of aluminium in the middle. The surface of the top layer that is facing the valve layer may for some materials be provided with so-called "peeling properties", which will help in opening the incisions or indentations provided in the valve layer and the top layer, but at the same time prevent the rest of the valve layer and the top layer from being ripped apart, when the valve layer and the top layer are moved relative to each other. A person skilled in the art will know how these properties can be obtained and are therefore not discussed any further.

The surface of the top layer that faces the bottom layer must be weldable, but need not have "peeling properties", in order to obtain a tight and durable weld connection between the top layer and bottom layer.

The bottom layer constitutes the bottom in the storage chamber for the product that is contained in the device and is normally manufactured from a barrier film, often with a thin sheet of aluminium arranged in the middle.

The surface of the bottom layer that faces the top layer must be weldable, but need not have "peeling properties", in order to obtain a tight and durable weld connection between the top layer and bottom layer.

The utility layer constitutes the other of the outer surfaces of the device, and serves in the same way as the front layer, to protect the layers being arranged on the inside from desiccation, and to prevent the user's hand or finger(s) from being soiled during the use of the device. In an embodiment of the present invention the utility layer may also be joined with an additional pocket layer in order to form a holding means for the device, which will ease the handling and use of the device. As the utility layer forms one of the liquid tight outer surfaces of the device, the utility layer may be manufactured from a liquid-impermeable material, for instance a plastic film that has good welding properties, in order to be attached to one or more of the other layers of the device. The attachment of the utility layer to the different layer(s) of the device may then for instance be done by means of heat-seal, ultrasonic weld or adhesive in order to prevent its removal from the other layer(s).

According to the present invention, the storage chamber, comprised of the top layer and the bottom layer, may also be manufactured as a multi chambered storage chamber, where this for instance is advantageous when the storage chamber contains two or more different products with different density and/or that the products are not to be mixed before the device is to be used. This "chambering" of the storage chamber may be achieved by at least one weld extending over the storage chamber, thereby dividing the storage chamber into a number of smaller chambers, the at least one weld forming a barrier between the different chambers. A number of flaps or tags (by providing incisions or indentations in the valve layer and top layer) are then provided in the vicinity of the at least one weld, on both sides of the at least one weld, where this arrangement will allow the different products to be mixed with each other when the through-going openings are provided in the storage chamber (the flaps or tags are fully opened by moving the valve layer relative to the top layer) and a certain pressure is applied to the device, prior to the use of the device.

It should be understood that the device according to the present invention also can comprise further additional layers.

The present invention relates to a device that contains a product, which device comprises a front layer and a utility layer which are welded together over a part of their outer periphery to form an outer protective surface of the device, where a contact layer is also welded between the front layer and utility layer, where a valve layer, a top layer and a bottom layer are arranged between the contact layer and the utility layer, the bottom layer being connected to the contact layer, the top layer and bottom layer being welded together by a weld to form a closed storage chamber in the device, where each of the valve layer and top layer further being provided with a plurality of incisions or indentations, the incisions or indentations being connected to each other, for instance by a weld, in order to form an opening mechanism in the device, where the movement of the valve layer relative to the contact layer/top layer will provide an opening of the incisions or indentations in the valve layer and top layer.

However, it should be understood that instead of being connected to the contact layer, the bottom layer can also be connected to the utility layer. Furthermore, the bottom layer may also be connected to both the contact layer and the utility layer. In an alternative embodiment the top layer may, instead of the bottom layer, be connected to the contact layer, the utility layer or to both contact layer and utility layer. All these embodiments will ensure that the valve layer, in order to open the device according to the present invention, can be moved relative to the top layer, as the top layer, either by itself or by the bottom layer, is connected to at least one of the other layers of the device.

Furthermore, a pocket layer is over at least a part of its outer edge connected to at least one of the other layers, where the pocket layer together with the utility layer will form an opening for a user's hand or finger(s). The pocket layer may for instance be manufactured from an elastic material.

In one embodiment of the present invention the incisions or indentations provided in the valve layer and top layer may have a drop-shaped form, but it is to be understood that other forms may also be utilized. Furthermore, the incisions or indentations are manufactured in such a way that the incisions or indentations will be connected with or be bound up with the valve layer and top layer. The incisions or indentations of the two layers will be cut out in such a way that the incisions or indentations in the valve layer will be opposite the incisions or indentations in the top layer, i.e. the end of the drop-shaped form of the incisions or indentations that is connected with or bound up with the valve layer will be arranged in an opposite way than the end of the drop-shaped form of the incisions or indentations that is connected with or bound up with the top layer. Furthermore, the incisions or indentations of the valve layer will have a greater extend than the incisions or indentations of the top layer. In addition, in order to obtain an even load or strain of the device when the valve layer is moved relative to the top layer, the valve layer and top layer are in most cases provided with an equal numbers of incisions or indentations.

The weld connecting the incisions or indentations of the valve layer and top layer comprises a closed weld seam arranged on the inside of the incisions or indentations of the valve layer and on the outside of the incisions or indentations of the top layer, thereby forming a closed sealing between the incisions or indentations of the valve layer and top layer, and a spot weld may be arranged within the closed weld seam. In an alternative embodiment of the present invention the whole area inside the incisions or indentations of the valve layer may be welded.

As explained above, each of the incisions or indentations of the valve layer and top layer will be connected or joined to their respective layers through a contact area, where this contact area is pre-impressed or stamped, where this will assist the opening and the "perforation" of the device according to the present invention.

For some applications of the device according to the present invention it is necessary that the contact layer, i.e. the layer that will apply the product contained in the device on a desired surface (and thereby also be in contact with the desired surface), for instance human skin, can be manufactured with a degree of roughness.

The bottom layer is joined or connected to the contact layer through a weld. However, it should be understood that the same is obtained by connecting the bottom layer to the utility layer, to both the contact layer and the utility layer, or instead of the bottom layer, that the top layer is connected to the contact layer, the utility layer or to both the contact layer and the utility layer. All these embodiments will ensure that the top layer is fixed to at least one of the other layers, thereby enabling the valve layer can be moved relative to the top layer, in order to allow the device to open.

In one embodiment of the device according to the present invention the front layer, contact layer and the utility layer are welded over a part of their outer periphery, forming an outer protective surface for the device and a partially "closed" device.

The foregoing and other objects, features and advantages of the invention will be apparent from the following more particular description of preferred non-limiting embodiments of the invention, as illustrated in the accompanying drawings:

FIGS. 7A-7B show how the device is opened, where FIG. 7A shows the manufactured device.

Figure 1A:
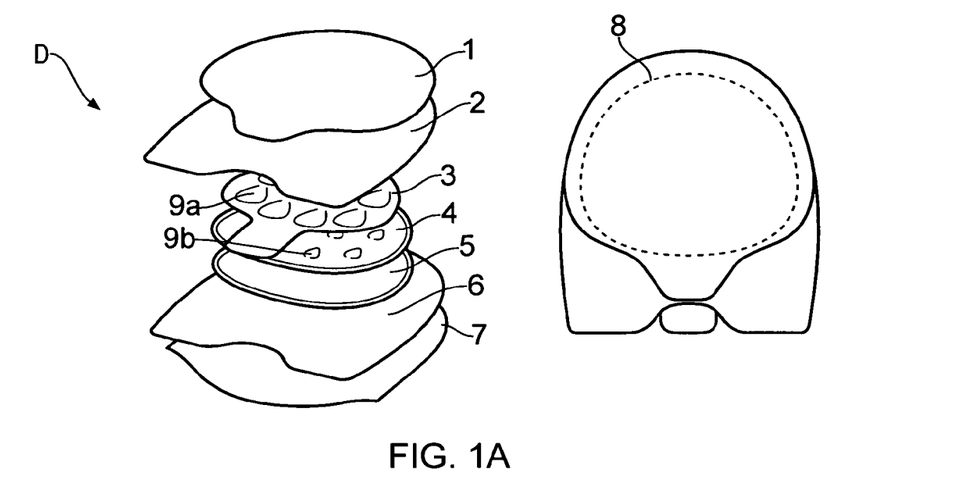
FIGS. 1A-1B illustrates a principal configuration of a device according to the present invention.
Figure 1B:
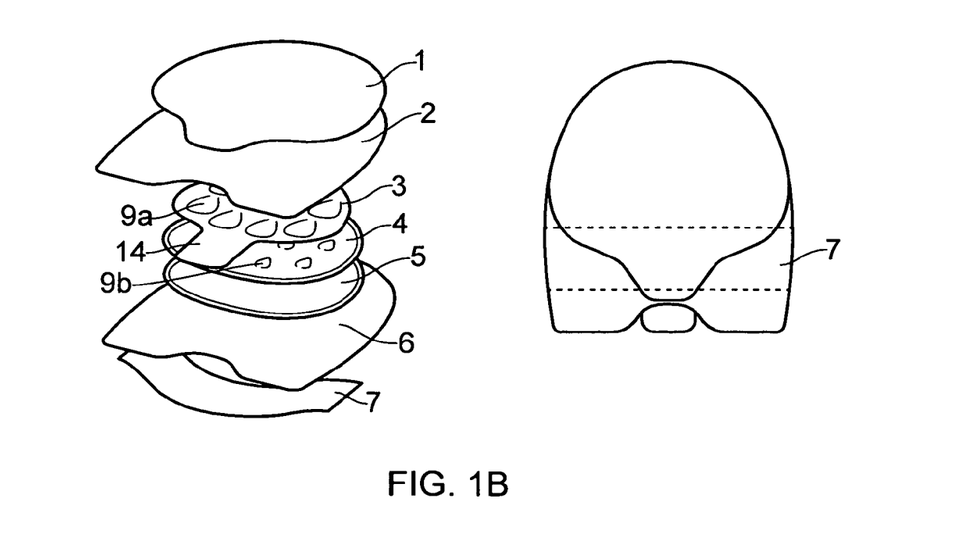

FIGS. 1A and 1B show a principal configuration of a device D according to the present invention. As can be seen, the device D is comprised of six different layers 1-6, where each layer has its own specific function.

However, it should be understood that the device may also be comprised of fewer or more layers, where the number of layers will depend on the specific use of the device, the materials and the product to be contained in the device.

An additional pocket layer 7 can be connected to a utility layer 6 in order to create a pocket or holding means in device D. This will ease the handling and use of the device D. The pocket layer 7 may be a layer having a similar form as the utility layer 6, or the pocket layer 7 may also be a band as shown in FIG. 1B.

A substantially impermeable front layer 1 and a utility layer 6 will form the outer, fluid-tight surfaces of the device D. Between the front layer 1 and the utility layer 6 are arranged a contact layer 2, a valve layer 3, a top layer 4 and a bottom layer 5. The front layer 1, the contact layer 2 and the utility layer 6 are then joined together around the outer periphery through a weld 10, in order to form the outer, fluid-tight surfaces of the device D. The weld 10 can be obtained by heat seal, laser, ultrasonic weld, adhesive, or combinations of these. Inside the front layer 1 and utility layer 6 are arranged the valve layer 3, top layer 4 and bottom layer 5, where these layers 3, 4, 5 will have a smaller degree of extension (area) than front layer 1, utility layer 6 and contact layer 2. This will result in that the layers 3, 4, 5 can be arranged "loosely" inside the device D.

Furthermore, the top layer 4 and bottom layer 5 are welded together around their outer peripheries in order to form a storage chamber 8 (see also FIG. 2) for the product that is to be accommodated in the device D. The weld can be seen as a weld seam 11 and can be performed by heat seal, laser, ultrasonic weld, adhesive or by combinations thereof.

Figure 2:
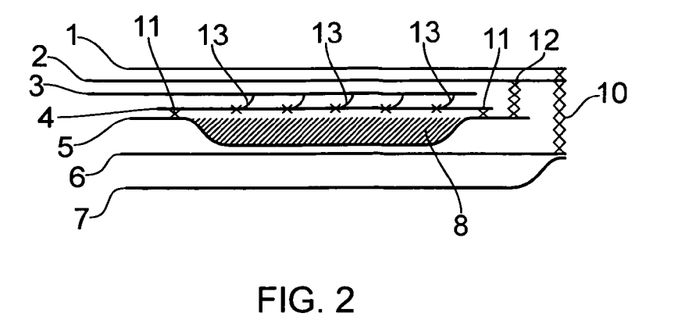
FIG. 2 shows a schematic cross section of the device in FIG. 1.

FIG. 2 shows a schematic cross section of the device D in FIG. 1, where it can be seen that the front layer 1, the contact layer 2 and utility layer 6, over at least a part of their outer periphery, are joined together through a weld seam 10, thereby forming the outer protective surface or barrier in the device D. Furthermore, in this embodiment a pocket layer 7 is also joined to the utility layer 6, the utility layer 6 and pocket layer 7 forming a pocket in the device D to ease the handling and use of the device D.

The top layer 4 and the bottom layer 5 which form the storage chamber 8 for the product that is to be accommodated in the device D, is connected to the contact layer 2 through a weld 12, where this will ensure that the storage chamber 8 is fixed to the contact layer 2 and the front layer 1 when the device D is to be opened before the use of the device D. The valve layer 3 is then attached or joined through a weld 13 to the top layer 4, where this shall be explained in detail below.

However, it should be understood that the bottom layer 5 may be connected to the utility layer 6, to both the contact layer 2 and the utility layer 6, or instead of the bottom layer 5, that the top layer 4 is connected to the contact layer 2, the utility layer 6 or to both the contact layer 2 and the utility layer 6. All these embodiments will ensure that the top layer 4 is fixed to at least one of the other layers 2, 6, thereby allowing the valve layer 3 to be moved relative to the top layer 4, in order to allow the device D to open.

Figure 3:
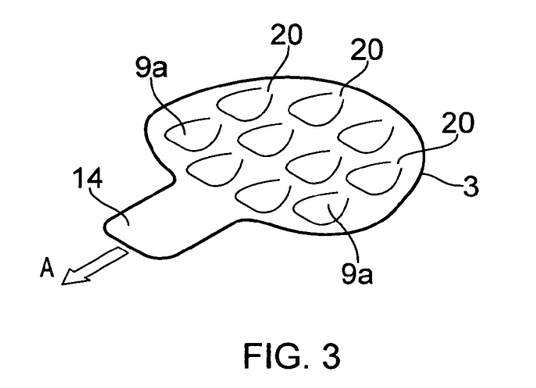
FIG. 3 shows details of a valve layer used in the device according to the present invention.

FIG. 3 shows the valve layer 3 in greater detail, where it can be seen that the surface of the valve layer 3 is provided with a plurality of incisions or indentations 9a. The incisions or indentations 9a are provided mechanically by use of a knife, a laser or ultra sound. With an incision or indentation 9a it should be understood that a cut is performed in the surface of the valve layer 3, where the cut is performed through the valve layer 3, but where the incision or indentation 9a through a contact area 20 will remain "hinged" to the valve layer 3. The incisions or indentations 9a will be opened when the valve layer 3 is moved relative to the top layer 4. The valve layer 3 is also designed with a flap 14, which flap 14 is used as a holding surface when the device D is to be open before use. An arrow A indicates in which direction the valve layer 3 has to be pulled in order to open the device D, see also FIGS. 7a and 7b and 8A-8D.

Figure 4:
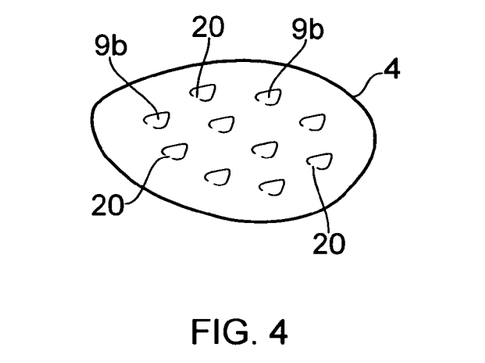
FIG. 4 shows details of a top layer used in the device according to the present invention.

FIG. 4 shows that also the top layer 4 is provided with a plurality of incisions or indentations 9b, where these incisions or indentations 9b are performed in the same way as the incisions or indentations 9a of the valve layer 3. However, it should be noted that the incisions or indentations 9b in the top layer 4 have an opposite form or design than the incisions or indentations 9a in the valve layer 3, i.e. that a finishing of one incision or indentation 9a (the area where the incision or indentation is stopped, i.e. the contact area 20) will correspond to a starting area (the area where the incision or indentation is started) of the incisions or indentations 9b when the valve layer 3 is arranged over the top layer 4. This can be seen in greater detail in FIGS. 5 and 6 and will be explained further below.

It is to be noted that the incisions or indentations 9a of the valve layer 3 have a greater extend (are larger) than the incisions or indentations 9b provided in the top layer 4. The incisions or indentations 9a, 9b have a drop-shaped form in the shown embodiment, but it should be understood that also other forms can be utilized in order to obtain the desired function for the opening of the device D before use. However, it is important that the incisions or indentations 9a, 9b in the valve layer 3 and top layer 4 are made in such a way that they correspond (the incisions or indentations 9a laying over the incisions or indentations 9b when the valve layer 3 is arranged over the top layer 4) to each other, as the incisions or indentations 9a, 9b are joined to each other through the weld 13.

Figure 5:
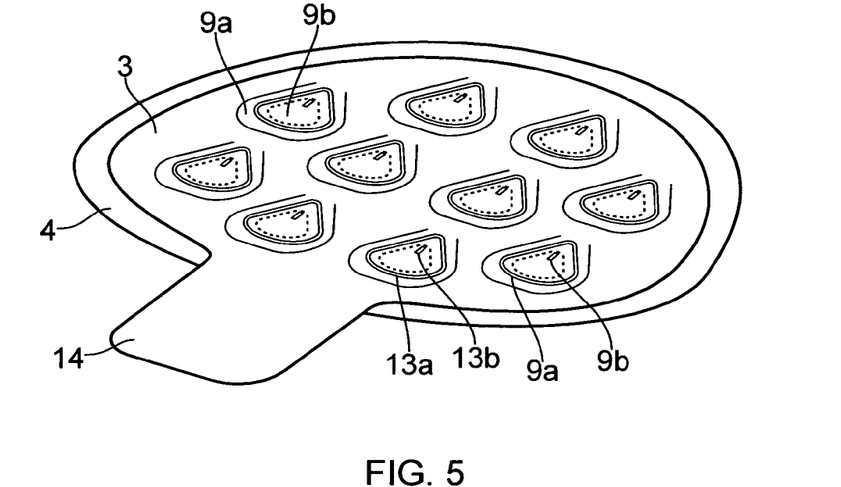
FIG. 5 shows how the valve layer and the top layer are connected to each other.

FIG. 5 shows how the valve layer 3 is arranged over the top layer 4, where the incisions or indentations 9a in the valve layer 3 are positioned over the incisions or indentations 9b in the top layer 4. As the incisions or indentations 9b have a smaller extend (are smaller) than the incisions or indentations 9a, the incisions or indentations 9b will be "laying" inside the contours of the incisions or indentations 9a.

When the valve layer 3 is arranged over the top layer 4, the incisions or indentations 9a, 9b are joined or connected to each other through a weld seam 13a and a spot weld 13b, the weld seam 13a and spot weld 13b together form the weld 13 shown in FIG. 2. Furthermore, the weld seam 13a is arranged between the inside of the incisions or indentations 9a and the outside of the incisions or indentations 9b, and will be a closed weld seam. The spot weld 13b is arranged in an area within both the incisions or indentations 9a, 9b.

Figure 6:
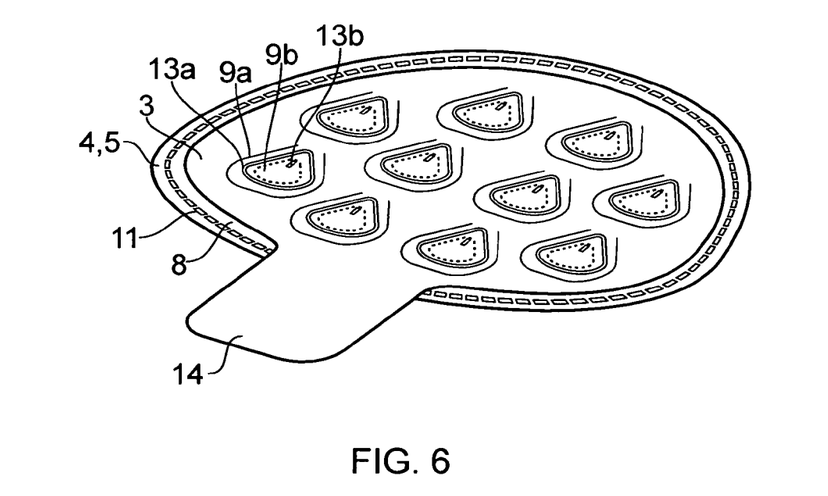
FIG. 6 shows how the valve layer, the top layer and a bottom layer are connected to each other in order to create a storage chamber in the device according to the present invention.

FIG. 6 shows how the storage chamber 8 that is to be accommodated when the product is created, as it can be seen that the valve layer 3 and the top layer 4 are arranged over the bottom layer 5. As explained in FIG. 5, the valve layer 3 and top layer 4 are joined or connected to each other through the weld 13, which is comprised of a weld seam 13a and possibly also a spot weld 13b, whereafter the top layer 4 is joined or connected to the bottom layer 5 through the weld 11. The weld 11 is arranged inside the outer periphery of the top layer 4 and bottom layer 5 and forms a closed circuit around the two layers 4, 5, whereby a storage chamber 8 is created inside the two layers 4, 5, see also FIG. 2.

Figure 7A:
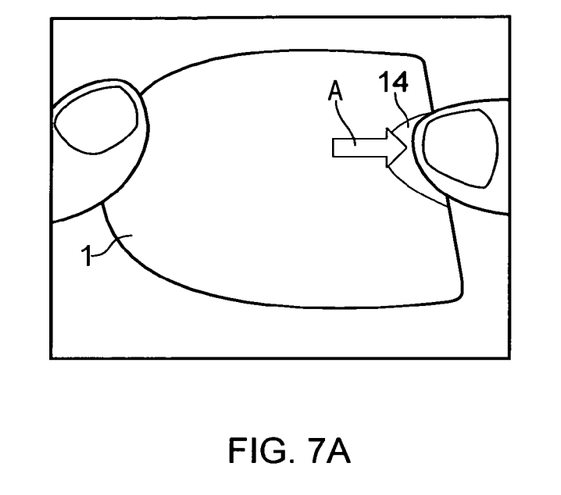
Figure 7B:
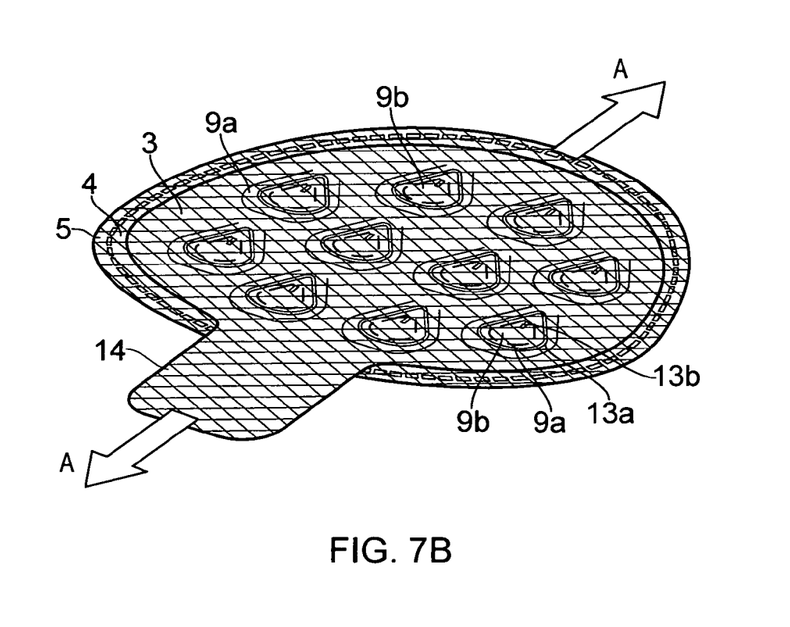
FIG. 7B shows only the storage chamber of the device (the front layer, a contact layer and the utilization layer are removed)

FIGS. 7a and 7b show how the device D is opened, as FIG. 7a shows a complete manufactured device D according to the present invention, while FIG. 7b shows only the valve layer 3 that is connected to the storage chamber 8 (formed by the top layer 4 and the bottom layer 5, in order to better show how the device is opened). When device D according to the present invention is to be used, the user will hold the outer peripheries of the device D with one hand, i.e. the front layer 1, the contact layer 2 (as the contact layer 2 is connected to the bottom layer 5 through the weld 12) and the utility layer 6 and will hold the flap 14 of the valve layer 3 with the other hand. When the valve layer 3 is pulled or dragged, i.e. moved relative to the top layer 4, the incisions or indentations 9a of the valve layer 3 will, after a certain force, start to open. If this movement of the valve layer 3 continues, the incisions or indentations 9a will start to open until fully opened, whereby the incisions or indentations 9b in the top layer 4 will follow the movement of the incisions or indentations 9a until the incisions or indentations 9b also are fully opened. Thus, the surface of the top layer 4 is opened, i.e. the incisions or indentations 9a, 9b are fully opened, whereby the product accommodated inside the storage chamber 8 can be squeezed out through the incisions or indentations 9a, 9b of the storage chamber 8 and through the contact layer 2 to be applied at the desired surface.

FIGS. 8A-8D illustrate in greater detail how the opening mechanism of the device according to the present invention works, i.e. when the valve layer 3 and top layer 4 are pulled in opposite directions (shown by arrows A).

Figure 8A:
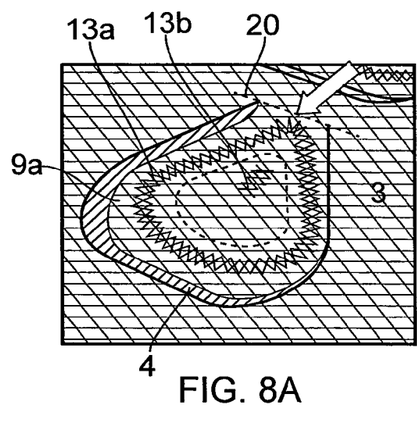
FIGS. 8A-8D show in greater detail how the opening mechanism of the device according to the present invention work.
Figure 8B:
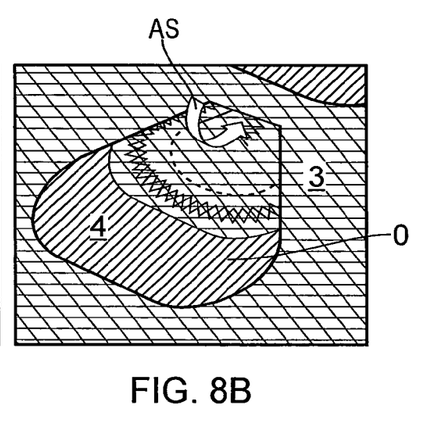

In FIG. 8A it can be seen that each of the incisions or indentations 9a of the valve layer 3 is "hinged" to the valve layer 3 through the contact area 20. The contact area 20 is mechanically pre-impressed or stamped, where this will ease the opening of this particular incision or indentation 9a. Furthermore, as the valve layer 3 in this figure is moved relative to the top layer 4, it is seen that the incision or indentation 9a has begun to open, as the incision or indentation 9a has begun to "roll" around the contact area 20. This can be seen in FIG. 8B, where an arrow AS indicates how the incision or indentation 9a is rolled under the valve layer 3 when the valve layer 3 is pulled in the direction of the arrow A in FIG. 7B. Furthermore, FIG. 8B shows that, due to the pulling of the valve layer 3, approximately a third of the incision or indentation 9a has been rolled under the valve layer 3, thereby providing an opening O in the valve layer 3.

Figure 8C:
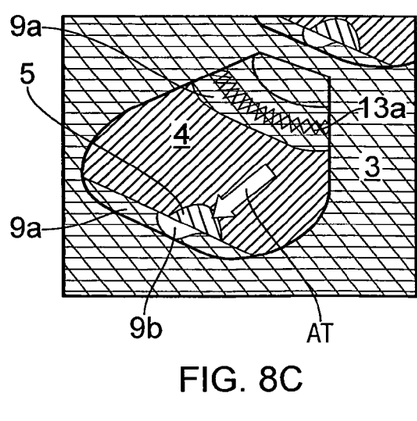

In FIG. 8C the incision or indentation 9a has been rolled further under the valve layer 3, where an arrow AT indicates the revealing of one incision or indentation 9b in the top layer 4. The incision or indentation 9b that is revealed is arranged in front of the incision or indentation 9a that is shown in FIGS. 8A and 8B, and it can be seen that also the incision or indentation 9b, being connected to the incision or indentation 9a through the weld 13a, 13b (see also FIG. 7B), has begun to open, whereby also the bottom layer 5 can be seen.

Figure 8D:
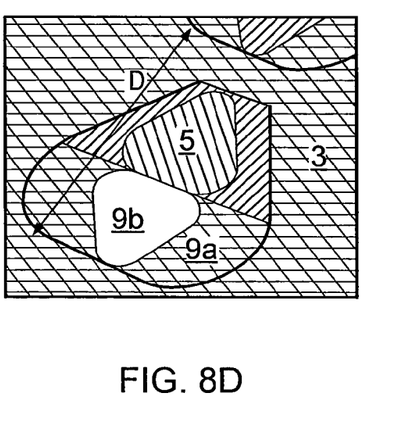

If the valve layer 3 is continued to be pulled in the arrow A's direction (shown in FIG. 7B), the whole incision or indentation 9b will eventually be revealed, as shown in FIG. 8D. Here it can be seen that the valve layer 3 has been pulled a distance D, which has resulted in the incision or indentation 9a of the valve layer 3 being rolled under the valve layer 3, where this rolling of the incision or indentation 9a has lead to the incision or indentation 9b of the top layer 4 having followed the rolling of the incision or indentation 9a thereby opening the top layer 4, such that the product accommodated in the storage chamber 8 can be delivered through the incisions or indentations of the top layer 4 and through the contact layer 2 in order to be applied onto a desired surface, for instance a human skin.

Further modifications and alternative embodiments of the present invention will be apparent to those skilled in the art in view of this description. Accordingly, this description is to be construed as illustrative only and is for purpose of teaching those skilled in the art the manner of carrying out the invention. It is to be understood that the forms of the invention shown and described herewith, are to be taken as the presently preferred embodiment. Various changes to the shape, size and arrangement of the different layers, may be made.

The invention claimed is:

1. A device (D) containing a product, which device (D) comprises a front layer (1) and a utility layer (6) being welded over a part of their outer periphery to form an outer protective surface of the device (D), a contact layer (2) also being welded between the front layer (1) and utility layer (6), characterized in that a valve layer (3), a top layer (4) and a bottom layer (5) are arranged between the contact layer (2) and utility layer (6), the top layer (4) and bottom layer (5) being welded together by a weld (11) to form a closed storage chamber (8) in the device (D), each of the valve layer (3) and top layer (4) being provided with a plurality of incisions or indentations (9a, 9b), the incisions or indentations (9a) of the valve layer (3) being connected to the incisions or indentations (9b) of the top layer (4) by a weld (13) to form an opening mechanism in the device (D) and the bottom layer (5) being connected to contact layer (2) and/or to the utility layer (6), where the movement of the valve layer (3) relative to the top layer (4) will provide an opening of the incisions or indentations (9a, 9b) in the valve layer (3) and top layer (4).

2. Device according to claim 1, characterized in that a pocket layer (7) over a part of its outer edges is connected to the other layers (1, 2, 6), the pocket layer (7) together with the utility layer (6) thereby forming an opening for a user's hand or finger(s).

3. Device according to claim 2, characterized in that the pocket layer (7) is manufactured from an elastic material.

4. Device according to claim 1, characterized in that the incisions or indentations (9a, 9b) have a drop-shaped form.

5. Device according to claim 4, characterized in that the incisions or indentations (9a) of the valve layer (3) have a greater extend than the incisions or indentations (9b) of the top layer (4).

6. Device according to claim 1, characterized in that the valve layer (3) and the top layer (4) are provided with an equal numbers of incisions or indentations (9a, 9b).

7. Device according to claim 1 or 6, characterized in that the weld (13) is comprised of a closed weld seam (13a) and a spot weld (13b).

8. Device according to claim 1, 4 or 6, characterized in that the incisions or indentations (9a, 9b) are only partly cut through the thickness of the valve layer (3) and top layer (4), thereby being connected or joined to the respective valve layer (3) and top layer (4) through a contact area (20).

9. Device according to claim 1, characterized in that the contact layer (2) has a surface with a degree of roughness.

10. Device according to claim 1, characterized in that the bottom layer (5) is joined or connected to the contact layer (2) through a weld (12).

11. Device according to claim 1, characterized in that the front layer (1), the contact layer (2) and the utility layer (6) are welded around their outer peripheries.

12. Device according to claim 1, characterized in that the storage chamber (8) is provided as a multi-chambered chamber.

* * * * *